United States Patent [19]

Lukacs, III

[11] Patent Number: 4,772,722

[45] Date of Patent: Sep. 20, 1988

[54] NADIMIDO-SUBSTITUTED CYCLOPHOSPHAZENE

[75] Inventor: Alexander Lukacs, III, Wilmington, Del.

[73] Assignee: Hercules Incorporated, Wilmington, Del.

[21] Appl. No.: 906,000

[22] Filed: Sep. 10, 1986

[51] Int. Cl.[4] .................................................. C07F 9/65
[52] U.S. Cl. ..................................... 548/413; 526/259; 526/262; 526/275; 528/321; 528/322; 548/407; 548/408; 548/410; 548/411
[58] Field of Search ................ 548/413, 410, 407, 408, 548/411

[56] References Cited

U.S. PATENT DOCUMENTS

| | | |
|---|---|---|
| 3,676,311 | 7/1972 | Frank et al. ...................... 204/159.14 |
| 3,711,389 | 1/1973 | Hook et al. ...................... 204/159.12 |
| 4,029,634 | 6/1977 | Meredith ............................ 260/45.9 |
| 4,258,172 | 3/1981 | Allcock et al. ..................... 528/168 |
| 4,550,177 | 10/1985 | Kumar et al. ........................ 548/413 |
| 4,568,498 | 2/1986 | Allen et al. .......................... 260/927 |

OTHER PUBLICATIONS

Kumar, D.; Fohlen, G. M.; Parker, J. A.; *J. Polymer Science, Polymer Chemistry Edition*, (1984), 22, 927–943.

Kumar, D.; Fohlen, G. M.; Parker, J. A.; *Macromolecules* (1983), 16, 1250–1257.

*Primary Examiner*—Harold D. Anderson
*Attorney, Agent, or Firm*—Joanne W. Patterson

[57] ABSTRACT

Disclosed are nadimido-substituted cyclophosphazene derivatives and thermosets thereof. The thermosets are useful as high temperature, flame resistant matrices for composites and as metal adhesives.

3 Claims, No Drawings

NADIMIDO-SUBSTITUTED CYCLOPHOSPHAZENE

FIELD OF THE INVENTION

This invention relates to new cyclophosphazene derivatives, and thermosets thereof having exceptional thermal and oxidative stability. This invention especially relates to thermosets of nadimido-substituted cyclophosphazenes that are useful as high temperature matrices for composites and as metal adhesives.

BACKGROUND OF THE INVENTION

Thermally stable polymers have many applications in the fields of adhesives, coatings, fibers and ablatives. The requirements for practical, thermally stable polymers include high melting (softening) temperatures, resistance to oxidative degradation at elevated temperatures, resistance to nonoxidative thermolytic processes, and stability to radiation and chemical reagents. These conditions are seldom met by organic polymers, where upper limits to thermal stability are generally in the area of 200° C. Compared with most organic polymers, inorganic polymers are generally stronger, harder, and exhibit the thermal and oxidative stability lacking in organic polymers. Unlike organic polymers, however, these materials usually are rather brittle, insoluble, and sometimes hydrolytically unstable.

For these reasons the study of polymers exhibiting both "organic" and "inorganic" properties has attracted wide attention, particularly the study of cyclic and open-chain phosphazene polymers. However, linear polymers have proved to be very expensive, since they must be prepared from cyclic halophosphazenes of high purity under exacting conditions.

SUMMARY OF THE INVENTION

New cyclophosphazene derivatives in which the phosphorus atoms are substituted by organic radicals terminating in a nadimido group have been prepared. Thermosets of these cyclophosphazene derivatives have the enhanced high temperature stability imparted by phosphazene rings, as well as the advantages of organic substituents.

The cyclophosphazene derivatives of this invention have the formula

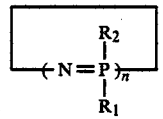

where n is 3 or 4; $R_1$ and $R_2$ are the same or different, may vary from one phosphorus atom to the next on the same cyclophosphazene ring and are selected from the group consisting of

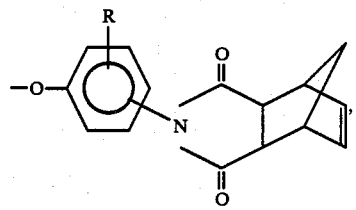

(a)

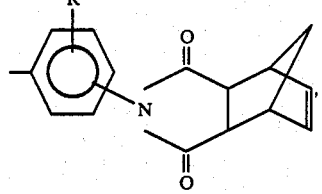

(b)

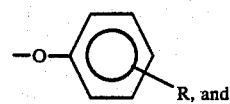

(c)

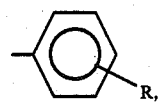

(d)

where R is selected from the group consisting of H or a nonreactive moiety; and an average of at least two of the radicals $R_1$ and $R_2$ per cyclophosphazene ring contain a nadimido group. Mixtures of phosphazene derivatives comprising at least 50% by weight of the cyclophosphazene derivative in which n=3 have also been prepared.

A thermostat cyclophosphazene polymer is prepared by heating the cyclophosphazene derivatives of this invention or a mixture of such cyclophosphazene derivatives, to form a melt and then raising the temperature from about 190° C. to about 350° C. for a time sufficient for thermosetting to occur. These materials can be used as high temperature adhesives for metals and as matrices for composites.

DETAILED DESCRIPTION OF THE INVENTION

The cyclophosphazene derivatives of this invention have the formula

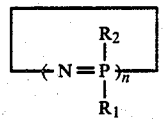

where n is 3 or 4 and $R_1$ and $R_2$ are the same or different, may vary from one phosphorus atom to the next on the same cyclophosphazene ring and are selected from the group consisting of

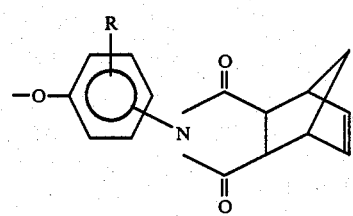

(a)

-continued (b) 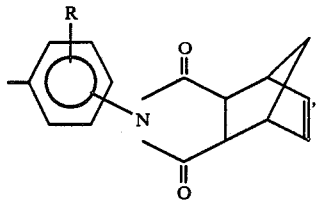

(c) 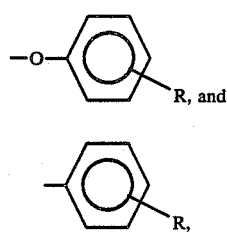
R, and (d) 
R, where R is selected from the group consisting of H or a nonreactive moiety. The average degree of substitution per cyclophosphazene ring by $R_1$ and $R_2$ radicals containing nadimido groups must be at least two. In this specification the term nadimido refers to a 3,6-endomethylene-1,2,3,6-tetrahydrophthalimido group.

The term nonreactive moiety refers to any substituent on the benzene ring that does not take part in a subsequent thermal polymerization and curing reaction. Such substituents include, for example, $-NO_2$, $-X$, $-R_3$, $-OR_3$, $$-\overset{O}{\underset{\|}{C}}-R_3,$$

$-CN$, $-CF_3$ or $-NR_3R_4$, where $R_3$ and $R_4$ are the same or different and are selected from the group consisting of hydrogen, a 1-4 carbon atom alkyl group and an aryl group, and X is halogen.

Exemplary of the readicals $R_1$ and $R_2$ where the benzene ring is substituted by such nonreactive moieties are 2-nitro-4-nadimidophenoxy, 3-nitro-5-nadimidophenyl, 4-nitrophenoxy, 3-nitrophenyl, 2-chloro-4-nadimidophenoxy, 3-chloro-5-nadimidophenyl, 4-bromophenoxy, 4-bromophenyl, 3-methyl-4-nadimidophenoxy, 4-methyl-3-nadimidophenyl, 4-methylphenoxy, 4-methylphenyl, 2-methoxy-4-nadimidophenoxy, 2-methoxy-4-nadimidophenyl, 4-methoxyphenoxy, 4-methoxyphenyl, 2-acetyl-4-nadimidophenoxy, 3-acetyl-5-nadimidophenyl, 4-acetylphenoxy, 3-acetylphenyl, 2-cyano-4-nadimidophenoxy, 3-cyano-5-nadimidophenyl, 4-cyanophenoxy, 3-cyanophenyl, 3-N,N-dimethyl-amino-5-nadimidophenoxy, 2-N,N-dimethylamino-4-nadimidophenyl, 4-N,N-dimethylaminophenoxy, 4-N,N-dimethylaminophenyl, 2-trifluoromethyl-4-nadimidophenoxy, 3-trifluoromethyl-5-nadimidophenyl, 4-trifluoromethylphenoxy, and 3-trifluoromethylphenyl.

Mixtures of the cyclotriphosphazene derivative and the analogous cyclotetraphosphazene derivative, as well as mixtures of these two cyclophosphazenes and higher cyclic analogues in which n is 5-12, can also be prepared. The mixtures containing the higher cyclic analogues may also contain small amounts of linear phosphazenes.

Cyclotriphosphazene derivatives are used to illustrate the reactions described below. However, any of the higher cyclic phosphazenes react in the same manner.

The cyclophosphazene derivatives of this invention can be prepared by partially substituting the halide in a halocyclophosphazene, e.g., compound 1, with a non-crosslinking organic radical to yield, for example, compound 2, followed by substitution of the remaining halide radicals by a nitro-substituted organic radical as in Reaction (1) below.

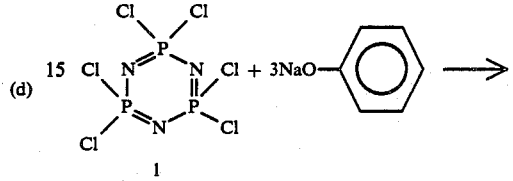

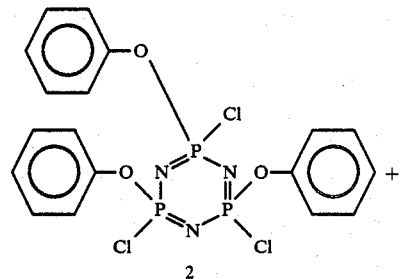

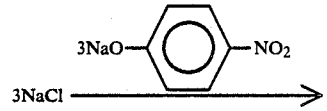

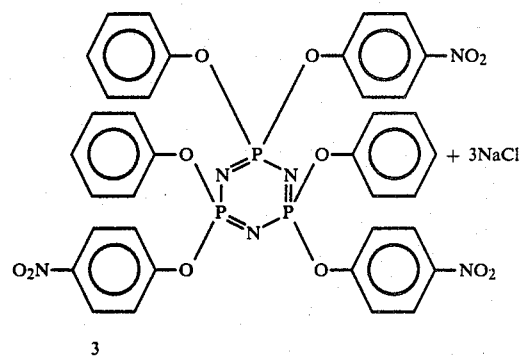

Reaction (1)

Alternatively, the entire complement of halides may be substituted by a nitro-substituted organic radical as in Reaction (2) below.

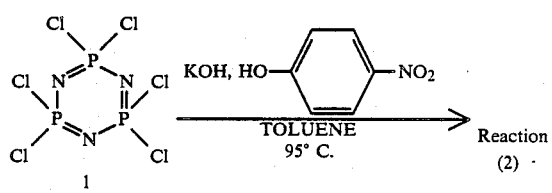

Reaction (2)

-continued

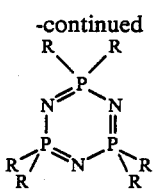

4

R = p-nitrophenoxy

The nitro groups of the cyclophosphazene derivative are then reduced to amine groups. Some or all of the resulting amine groups are reacted with 5-norbornene-2,3-dicarboxylic anhydride. Initial addition of the anhydride at an amine group is followed by a cyclodehydration step at about 165° C. which yields the nadimido-substituted cyclophosphazene via Reaction (3) below. The notation DMAC refers to N,N-dimethylacetamide.

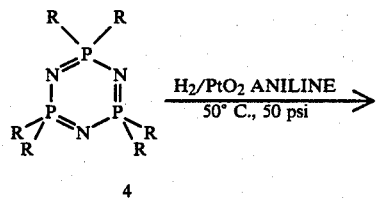

4

R = p-nitrophenoxy

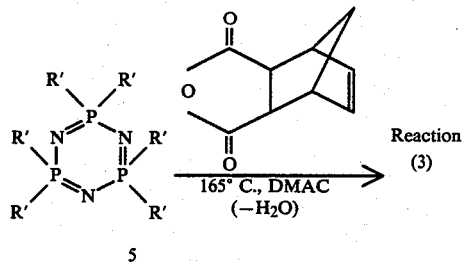

Reaction (3)

5

R′ = p-aminophenoxy

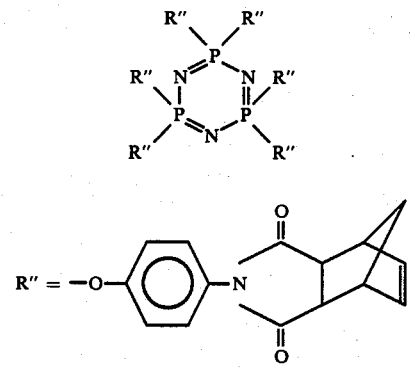

6

R″ = —O—⟨phenyl⟩—N⟨norbornene-dicarboximide⟩

Cyclophosphazene derivatives in which all of the phosphorus atoms are substituted by nadimidophenoxy radicals, or in which half of the phosphorus atoms are substituted with nadimidophenoxy radicals and half are substituted with phenoxy radicals, are preferred.

Thermosets are prepared by heating the cyclophosphazene derivatives of this invention, or mixtures of these cyclophosphazene derivatives, to the melting point and then raising the temperature from about 190° C. to about 350° C. for a time sufficient for thermosetting to occur.

A typical cure cycle for thermosetting hexakis-(p-nadimidophenoxy)cyclotriphosphazene consists of heating the cyclotriphosphazene derivative until a phase change from a white solid to a red, viscous liquid occurs, holding the liquid at 190° C. to 230° C. for two hours, raising the temperature to 260° C. to 350° C. and maintaining this temperature for another two hours. The material is then post-cured at 260° C. to 350° C. for about sixteen hours.

Although the mechanism of the cure is not fully understood, it is believed to proceed via an initial reverse Diels-Alder reaction at the nadimide termini followed by an addition polymerization involving the resulting maleimide and cyclopentadiene moieties as in Reaction (4) below.

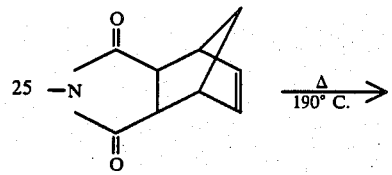

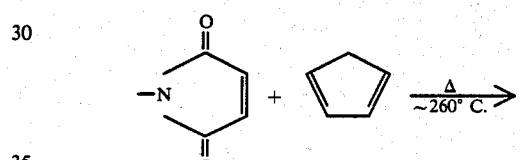

Reaction (4)

Although the new cyclophosphazene derivatives of this invention can be prepared from pure halocyclophosphazenes, it has been found that thermosets of comparable thermal and oxidative stability that are considerably less expensive can be obtained by using commercially available ("technical grade") hexachlorocyclotriphosphazene (an 80/20 mixture of hexachlorocyclotriphosphazene/octachlorocyclotetraphosphazene) as the starting material. Suitable starting materials also include mixture comprising at least 50% by weight halocyclotriphosphazene, as well as halocyclotetraphosphazene, halogenated higher cyclic analogues in which n is 5 to 12, and possibly small amounts of halogenated linear phosphazenes. These mixtures typically contain less than 10% halogenated linear phosphazenes and less than 25% cyclic analogues in which n is 5 to 12. It is understood that whenever reference is made in this specification to mixtures comprising at least 50% of the cyclotriphosphazene derivative, these mixtures also contain the analogous cyclotetraphosphazene derivative and may also contain higher cyclic analogues and small amounts of linear phosphazenes.

The thermosets prepared from the cyclophosphazene derivatives of this invention have exceptional thermal and oxidative stability. No weight losses are observed at temperatures below 350° C., while only minor (10–25%) weight losses can be detected in the temperature range 350° C. to 425° C. (N$_2$ or air purge). For the polymers resulting from polymerization of hexakis(p-nadimidophenoxy)cyclotriphosphazene, a 30% loss is observed between 425° C. and 1000° C. (N$_2$ purge). This results in a 58% char yield at 1000° C. In air, a 30% weight loss is noted between 425° C. and 700° C., at which temperature extensive oxidation degradation ensues. Similar profiles are observed for the other cyclophosphazene derivatives.

The cyclophosphazene thermosets can be used in aircraft and automotive applications for bonding any structural metal or alloy, but are particularly useful for bonding aluminum and titanium surfaces. The metal surfaces to be bonded can be first subjected to a pretreatment such as acid etching or grit blasting before the application of the adhesive. The details of such treatments depend upon the metal being bonded and the use of the final structure and are well known to those skilled in the art. The adhesive is usually applied in liquid or meltable-film form, but can also be applied in powder form to a woven scrim that is placed between the surfaces to be bonded. The adhesive is typically heated to cure it while pressure is applied.

The cyclophosphazene thermosets can also be used as matrices for composites, in the preparation of laminates and as corrosion resistant coatings for metals.

The following examples are illustrative of the invention and are not intended to limit its scope in any way. All parts and percentages are by weight unless otherwise specified.

EXAMPLE 1

Synthesis of Hexakis-(p-nadimidophenoxy)cyclotriphosphazene (Compound 6)

Methods for preparing the hexakis-(p-aminophenoxy)cyclotriphosphazene starting material, compound 5, are known in the art, for example, as described in U.S. Pat. No. 4,550,177. Granular 5-norbornene-2,3-dicarboxylic anhydride (8.86 g, 0.054 moles) is added to a stirred solution of compound 5 (7.09 g, 0.009 moles) in 75 mls N,N-dimethylacetamide. The light brown solution is heated under a nitrogen atmosphere to 160° C. for three hours. After this time the reaction mixture is cooled to room temperature, poured over crushed ice and macerated until stirring becomes difficult. The resulting solid is filtered from the ice slurry and washed several times with water, methanol and finally diethyl ether to yield 11.68 g (77% yield) of a white solid. The structure of compound 6 and the compounds prepared in the following examples are determined from $^{31}$P NMR spectra at a field strength of 146 MHz, $^1$H NMR spectra at a field stregth of 90 MHz, and elemental analysis. $^1$H NMR(DMSO-d$_6$) δ6.8 (24H multiplet, aromatic), 6.1(12H singlet, vinyl), 3.3(12H singlet, bridgehead), 3.2(12H singlet, bridgehead), 1.5(12H singlet, methylene); $^{31}$P NMR(DMSO) δ9.4(singlet).

EXAMPLE 2

Thermal Polymerization of Hexakis-(p-nadimidophenoxy)cyclotriphosphazene (Compound 6)

A 0.5 g sample of hexakis(p-nadimidophenoxy)cyclotriphosphazene 6 is heated to 200° C. in an aluminum pan under nitrogen. The sample melts to a viscous, red liquid at approximately 160° C. The temperature is held at 200° C. for two hours. The temperature is then raised slowly to 300° C. Slow cooling yields a dark red, glassy polymer.

The thermal properties of the polymer are determined using thermogravimetric analysis in air and nitrogen. The polymer decomposition temperature (PDT), the temperature at which the polymer's maximum rate of weight loss occurs (PDT$_{max}$) and the char yields both in air and nitrogen, are given in the table following Example 11.

EXAMPLE 3

Synthesis of a Mixture of Tris(phenoxy)tris(p-nitrophenoxy)cyclotriphosphazene (Compound 3) and Tetrakis-(phenoxy)tetrakis(p-nitrophenoxy)cyclotetraphosphazene A solution of "technical grade" hexachlorocyclotriphosphazene (99.7 g, 0.86 moles of NPCl$_2$ units) in 575 mls tetrahydrofuran is added to a three liter, three-necked flask. The flask is equipped with an overhead stirrer and reflux condenser. As indicated previously, "technical grade" is a commercially available 80/20 mixture of hexachlorocyclotriphosphazene/octachlorocyclotetraphosphazene.

A solution of sodium phenoxide is prepared by slowly adding a solution of phenol (80.89 g, 0.86 moles) in 175 mls tetrahydrofuran to a slurry of sodium hydride (34.4 g of a 60% mineral oil dispersion, 0.86 moles) in 175 mls tetrahydrofuran at 0° C. This solution is added dropwise to the phosphazene solution, which is also maintained at 0° C. The reaction mixture is refluxed for forty-eight hours. The resulting solution is cooled in ice.

A solution of sodium nitrophenoxide is prepared by slowly adding a solution of 4-nitrophenol (119.6 g, 0.86 moles) in 285 mls tetrahydrofuran to a cooled slurry of sodium hydride (34.4 g of a 60% mineral oil dispersion, 0.86 moles) in 285 mls tetrahydrofuran. This solution is slowly added to the flask containing the phosphazene mixture. The resulting solution is refluxed for sixty-five hours. After this time the reaction mixture is cooled, filtered to remove sodium chloride and washed with hot tetrahydrofuran. The filtrate is concentrated, poured over crushed ice and macerated. The gummy oil is washed with large quantities of water and methanol, and dried in a desiccator to yield 71.6 g of a light brown solid (30% yield based on the phosphazene starting material). $^{31}$P NMR (DMSO) δ8.8(m), δ-12.8 (m); $^1$H NMR (DMSO-d$_6$) δ8.1 (d, J=7 Hz), δ7.4–6.7 (unresolved), relative intensities 1:5.

EXAMPLE 4

Reduction of the Mixture of Tris(phenoxy)tris(p-nitrophenoxy)cyclotriphosphazene (Compound 3) and Tetrakis(phenoxy)tetrakis(p-nitrophenoxy)-cyclotetraphosphazene to a Mixture of Tris(phenoxy)tris(p-aminophenoxy)cyclotriphosphazene and Tetrakis-(phenoxy)tetrakis(p-aminophenoxy)cyclotetraphosphazene A Fisher-Porter hydrogenation apparatus is charged with a mixture of tris(phenoxy)tris(p-nitrophenoxy)cyclotrisphosphazene 3 and tetrakis(phenoxy)tetrakis(p-nitrophenoxy)cyclotetraphosphazene

[50.00 g, 0.18 moles of

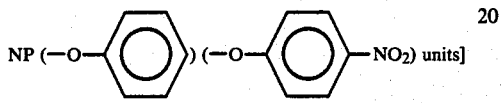

units]

and 125 mls aniline which contains 0.236 g platinum oxide catalyst. The mixture is agitated and heated to 90° C. under 50 psi of hydrogen pressure. The reduction is allowed to continue until hydrogen consumption ceases. The mixture is then cooled and filtered. The filtrate is concentrated and poured into stirred cyclohexane (500 mls). A light brown solid precipitates. The cyclohexane is decanted off and the solid allowed to air dry overnight. Recrystallization from o-dichlorobenzene results in isolation of 19.99 g of product (45% yield based on the phosphazene starting material). $^{31}$P NMR (DMSO) δ9.6 (s), δ-11.7 (s); $^1$H NMR (CDCl$_3$) δ7.3–6.3 (unresolved), δ3.6 (br s), relative intensities 9:2.

EXAMPLE 5

Synthesis of a Mixture of Tris(phenoxy)tris(p-nadimidophenoxy)cyclotriphosphazene and Tetrakis-(phenoxy)tetrakis(p-nadimidophenoxy)cyclotetraphosphazene Granular 5-norbornene-2,3-dicarboxylic anhydride (3.28 g, 0.02 moles) is added to a stirred solution of tris(phenoxy)tris(p-aminophenoxy)cyclotriphosphazene and tetrakis(phenoxy)tetrakis(p-aminophenoxy)-cyclotetraphosphazene

[4.92 g, 0.02 moles based on

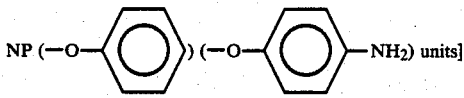

units]

in 75 mls N,N-dimethylacetamide. The brown mixture is heated to 160° C. under a nitrogen atmosphere for three hours. The mixture is then cooled, poured over crushed ice and macerated. The resulting solid is filtered from the ice slurry and washed with water, methanol, and diethyl ether. After drying, 5.80 g of a light brown solid is recovered (74% yield). $^1$H NMR(DMOS-d$_6$) δ7.3–6.7(aromatic), 6.2(vinyl), 3.3(bridgehead), 3.2(bridgehead), 1.6(methylene); $^{31}$P NMR(DMSO) δ9.2(singlet), −11.8(singlet).

EXAMPLE 6

Thermal Polymerization of a Mixture of Tris(phenosy)tris(p-nadimidophenoxy)cyclotriphosphazene and Tetrakis-(phenoxy)tetrakis(p-nadimidopheoxy)cyclotetraphosphazene A 0.5 g sample of a mixture of tris(phenoxy) tris(p-nadimidophenoxy)cyclotriphosphazene and tetrakis-(phenoxy)tetrakis(p-nadimidophenoxy)cyclotetraphosphazene is polymerized using the procedure described in Example 2. The product is a dark red, glassy polymer. The thermal properties of the polymer are given in the Table following Example 11.

EXAMPLE 7

Synthesis of 2,2,4,4-Tetra(p-nitrophenoxy)-6,6-diphenylcyclotriphosphazene

Methods for preparing 2,2,4,4-tetrachloro-6,6-diphenylcyclotriphosphazene are known in the art. For example, see K. A. Shaw et al, J. Chem. Soc., 121 (1964).

A solution of sodium p-nitrophenoxde (15.46 g, 0.096 moles) in 100 mls tetrahydrofuran is added dropwise to a stirred solution of 2,2,4,4-tetrachloro-6,6-diphenylcyclotriphosphazene (10.25 g, 0.024 moles) in 80 mls of tetrahydrofuran. The reaction mixture is then refluxed under a nitrogen atmosphere for 72 hours. After six hours the reaction mixture changes from bright orange to yellow. Sodium p-nitrophenoxide (7.73 g, 0.048 moles) and 15 mls of tetrahydrofuran are again added at this point, turning the mixture orange again.

After 72 hours the reaction mixture is cooled to room temperature and filtered. A precipitate forms after adding 300 mls water to the filtrate. The precipitate is filtered, washed with water and finally with ethanol. A white solid is recovered (17.76 g, 88% yield). $^1$H NMR(acetone-d$_6$) δ8.1(8H doublet, aromatic), 7.7–7.3(18H unresolved, aromatic); $^{31}$P NMR(CHCl$_3$) δ23.1(triplet), 3.3(doublet).

EXAMPLE 8

Preparation of 2,2,4,4-Tetra-(p-aminophenoxy)-6,6-diphenylcyclotriphosphazene 2,2,4,4-Tetra(p-nitrophenoxy)-6,6-diphenylcyclotriphosphazene (16.01 g, 0.021 moles), platinum oxide catalyst (0.09 g, 0.0004 moles), and 50 mls aniline are added to a 500 ml Fischer-Porter reaction vessel. The reaction is heated to 50° C. at 50–60 psi of hydrogen pressure for 65 hours. The reaction mixture is then cooled and concentrated to about 25 mls under vacuum. The concentrate is poured into 250 mls cyclohexane, and a brown coagulate forms. The solvent is decanted off and the residue is poured into hot cyclohexane and allowed to cool until stirring becomes difficult. The solvent is decanted off and the residue chilled for about 20 minutes. Recrystallization from o-dichlorobenzene yields a pale brow precipitate, which is boiled in cyclohexane for two hours. A solid is recovered (10.8 g, 78% yield). $^{31}$P NMR (THF) δ21.3(triplet), 10.1(doublet).

EXAMPLE 9

Preparation of 2,2,4,4-Tetra(p-nadimidophenoxy)-6,6-diphenylcyclotriphosphazene Granular 5-norbornene-2,3-dicarboxylic anhydride (5.04 g, 0.031 moles) is added to a stirred solution of 2,2,4,4-tetra(p-aminophenoxy)-6,6-diphenylcyclotriphosphazene (5.01 g, 0.007 moles) in 100 mls dimethylacetamide. The reaction mixture is refluxed under nitrogen for 3.5 hours. The mixture is then poured into ice, and a white precipitate forms. After filtering the precipitate is washed with water and then with methanol. After drying overnight in a desiccator, 7.51 g of product is recovered (82% yield). $^1$H NMR(acetone-$d_6$) $\delta$7.4–7.1(10H, aromatic), 7.0–6.8(16H, aromatic), 6.2(8H singlet, vinyl), 3.4(8H singlet, bridgehead), 3.3(8H singlet, bridgehead), $\delta$1.6(8H singlet, methylene); $^{31}$P NMR(acetone) $\delta$22.6(triplet), 8.9 (doublet).

EXAMPLE 10

Thermal Polymerization of 2,2,4,4-Tetra(p-nadimidophenoxy)-6,6-diphenylcyclotriphosphazene A 0.5 g sample of 2,2,4,4-tetra(p-nadimidophenoxy)-6,6-diphenylcyclotriphosphazene is polymerized using the procedure described in Example 2. The product is a dark red, glassy polymer. The thermal properties of the polymer are given in the Table following Example 11.

EXAMPLE 11

Adhesion Testing of the Thermoset Prepared from Hexakis(p-nadimidophenoxy)cyclotriphosphazene (Compound 6)

Lap shear specimens are fabricated using acid-etched aluminum as the adherend. The adhesive in powder form is applied to a woven fiberglass scrim and placed between two sheets of aluminum with a ½ inch overlap. The sheets are bonded in a hydraulic press under a 60 psi pressure with the following cure schedule; 80 min to 94° C.; 50 min to 210° C.; 100 min at 210° C.; 50 min to 315° C.; 100 min at 315° C. The sample is post-cured at 295° C. for six hours. Lap shear tests are conducted according to ASTM-D1002 at 25° C. Bond failure is cohesive, i.e. within the adhesive layer, at a shear strength of 420 psi. Adhesive bonding of the polymer to the metal surfaces is maintained.

TABLE

| | Thermal Properties of Cyclophosphazene Polymers | | | | | | | |
|---|---|---|---|---|---|---|---|---|
| | In nitrogen | | | | In air | | | |
| | PDT | PDT$_{max}$ | Char yield % | | PDT | PDT$_{max}$ | Char yield % | |
| Polymer | (°C.) | (°C.)(*W) | 800° C. | 2500° C. | (°C.) | (°C.)(*W) | 700° C., | 800° C. |
| (1) | 400 | 410(89) | 68 | 48** | 400 | 410(89) | 56 | 28 |
| (2) | 385 | 400(85) | 67 | — | — | — | — | — |
| (3) | 370 | 410(90) | 75 | — | — | — | — | — |
| (4) | 370 | 405(84) | 60 | — | — | — | — | — |

(1) Polymer of hexakis(p-nadimidophenoxy)cyclotriphosphazene
(2) Polymer of tris(phenoxy)tris(p-nadimidophenoxy)cyclotriphosphazene
(3) Polymer prepared from a mixture of tris(phenoxy)tris(p-nadimidophenoxy)-cyclotriphosphazene and tetrakis(phenoxy)tetrakis(p-nadimidophenoxy)-cyclotetraphosphazene
(4) Polymer of 2,2,4,4-tetra(p-nadimidophenoxy)-6,6-diphenylcyclotriphosphazene
*W = weight remaining at the PDT$_{max}$ indicated
**Black, glassy, honeycombed char

What I claim and desire to protect by Letters Patent is:

1. A cyclophosphazene derivative having the formula $$\left( N=\underset{R_1}{\overset{R_2}{P}} \right)_n$$

where n is 3 or 4; $R_1$ and $R_2$ are the same, different, or vary from one phosphorus atom to the next on the same cyclophosphazene ring and are selected from the group consisting of (a), (b), (c), and (d) [structural formulas shown]

where R is selected from the group consisting of H or a nonreactive moiety; and an average of at least two of the radicals $R_1$ and $R_2$ per cyclophosphazene ring contain a nadimido group.

2. The cyclophosphazene derivative of claim 1 wherein all of the radicals $R_1$ and $R_2$ are nadimidophenoxy radicals.

3. The cyclophosphazene derivative of claim 1 wherein half of the radicals $R_1$ and $R_2$ are phenoxy radicals and the remaining radicals $R_1$ and $R_2$ are nadimidophenoxy radicals.

* * * * *

UNITED STATES PATENT AND TRADEMARK OFFICE
CERTIFICATE OF CORRECTION

PATENT NO. : 4,772,722

DATED : September 20, 1988

INVENTOR(S) : LUKACS 1

It is certified that error appears in the above-identified patent and that said Letters Patent is hereby corrected as shown below:

Column 2, Line 30

"thermostat" should read --thermoset--

Column 3, Line 41

"readicals" should read --radicals--

Column 5, Line 61

"6" is omitted and should be inserted in patent

UNITED STATES PATENT AND TRADEMARK OFFICE
CERTIFICATE OF CORRECTION

PATENT NO. : 4,772,722
DATED : September 20, 1988
INVENTOR(S) : LUKACS 1

It is certified that error appears in the above-identified patent and that said Letters Patent is hereby corrected as shown below:

Column 6, Lines 41 and 44

" 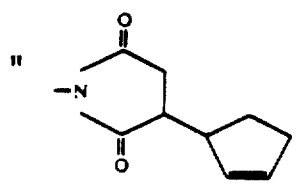 "  should be  -- 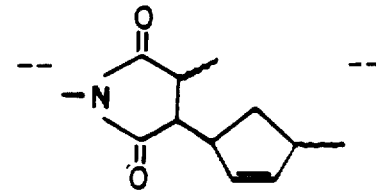 --

Column 6, Line 52

"(" should be omitted from patent

Column 6, Line 55

"mixture" should read --mixtures--

UNITED STATES PATENT AND TRADEMARK OFFICE
CERTIFICATE OF CORRECTION

PATENT NO. : 4,772,722

DATED : September 20, 1988

INVENTOR(S) : LUKACS 1

It is certified that error appears in the above-identified patent and that said Letters Patent is hereby corrected as shown below:

Column 10, Line 4

"(phenosy)"   should read   --(phenoxy)--

Column 10, Line 6

"(p-nadimidopheoxy)"   should read   --(p-nadimidophenoxy)--

Column 11, Line 41

"schedule;"   should read   --schedule:--.

Signed and Sealed this

Seventh Day of February, 1989

*Attest:*

DONALD J. QUIGG

*Attesting Officer*        *Commissioner of Patents and Trademarks*